(12) United States Patent
Fiard et al.

(10) Patent No.: US 12,623,032 B2
(45) Date of Patent: May 12, 2026

(54) SAFETY DEVICE FOR SHIELDING AN INJECTION NEEDLE OF A MEDICAL CONTAINER, AND AN INJECTION DEVICE INCLUDING THIS SAFETY DEVICE

(71) Applicant: Becton Dickinson France, Le Pont de Claix (FR)

(72) Inventors: Michael Fiard, Eybens (FR); Henry-Gilles Chaniol, Fontanil-Cornillon (FR); Gregory Peruzzo, Prunieres (FR)

(73) Assignee: Becton Dickinson France, Le Pont de Claix (FR)

( * ) Notice: Subject to any disclaimer, the term of this patent is extended or adjusted under 35 U.S.C. 154(b) by 687 days.

(21) Appl. No.: 18/087,944

(22) Filed: Dec. 23, 2022

(65) Prior Publication Data

US 2023/0201473 A1     Jun. 29, 2023

(30) Foreign Application Priority Data

Dec. 24, 2021     (EP) ..................................... 21306937

(51) Int. Cl.
*A61M 5/32* (2006.01)

(52) U.S. Cl.
CPC .......... *A61M 5/3245* (2013.01); *A61M 5/326* (2013.01)

(58) Field of Classification Search
CPC .. A61M 5/326; A61M 5/3243; A61M 5/3245; A61M 2005/3261
See application file for complete search history.

(56) References Cited

U.S. PATENT DOCUMENTS

| | | | |
|---|---|---|---|
| 6,319,233 B1 | 11/2001 | Jansen et al. | |
| 6,679,864 B2 | 1/2004 | Gagnieux et al. | |
| 6,918,889 B1 * | 7/2005 | Brunel ................. | A61M 5/326 |
| | | | 604/110 |
| 9,022,989 B2 | 5/2015 | Bicknell et al. | |
| 2003/0212380 A1 | 11/2003 | Barrelle | |
| 2020/0316311 A1 | 10/2020 | Holland et al. | |

FOREIGN PATENT DOCUMENTS

WO            02098494 A2    12/2002

* cited by examiner

*Primary Examiner* — Nilay J Shah
(74) *Attorney, Agent, or Firm* — The Webb Law Firm

(57) ABSTRACT

A safety device includes a tubular body, a needle cover, a release element, and a retainer. The tubular body extends along a longitudinal axis and is configured to receive a medical container. The needle cover is movable relative to said body between a retracted position and a distally extended position to shield the injection needle after activation of the safety device. The release element is configured to move the needle cover from the retracted to the extended position. The retainer is configured to transmit a user's activation force to the needle cover once the injection operation is completed. The needle cover includes a distal abutment surface abutting against a proximal abutment surface of a bump protruding from the body in the retracted position. The body has a first axial slot extending from a distal end of the body, and the bump is circumferentially distant from said first axial slot.

15 Claims, 11 Drawing Sheets

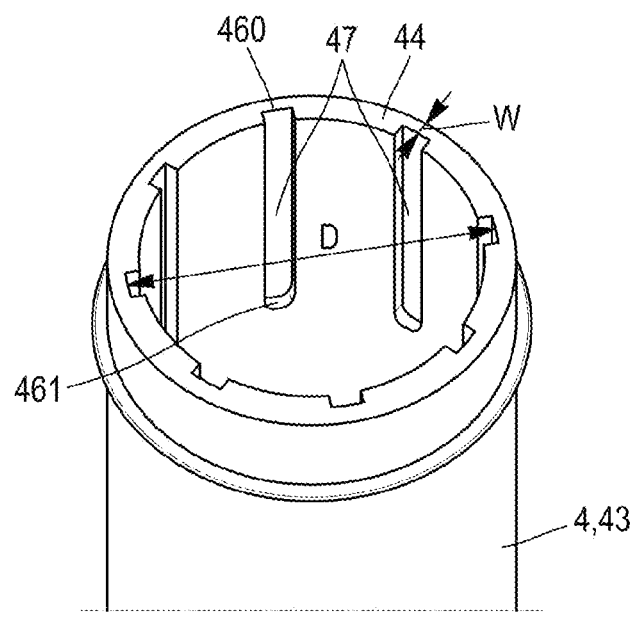
FIG. 3
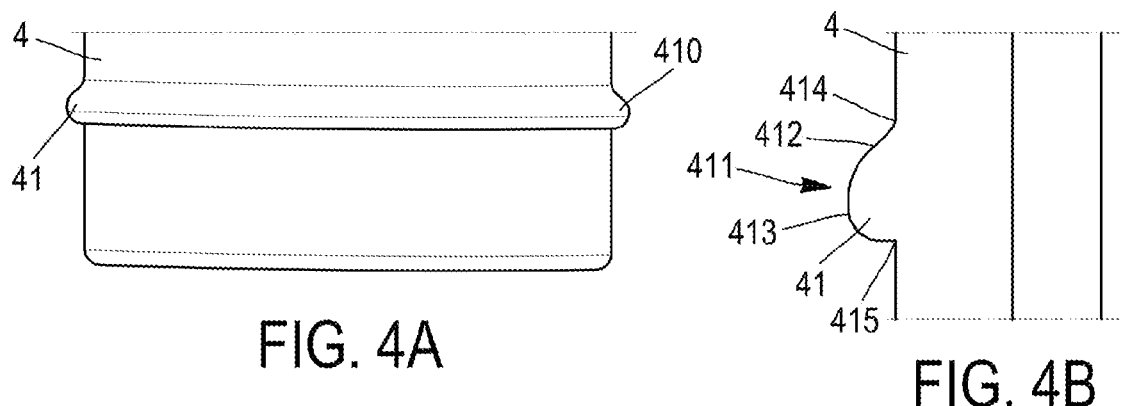
FIG. 4A
FIG. 4B
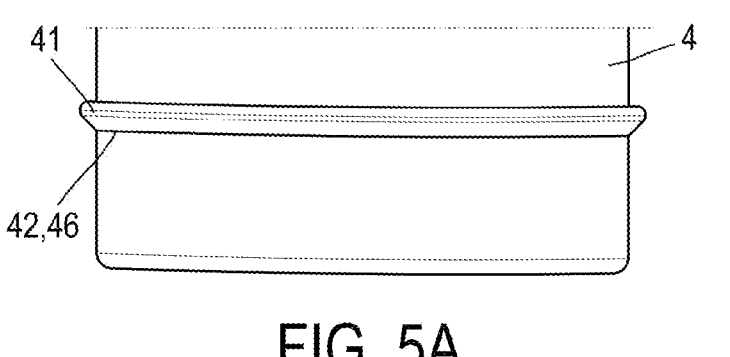
FIG. 5A
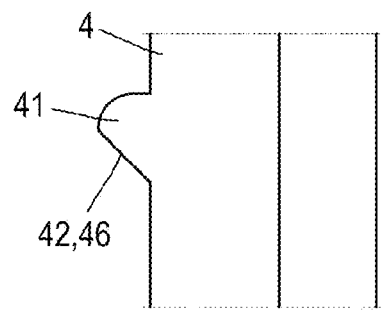
FIG. 5B

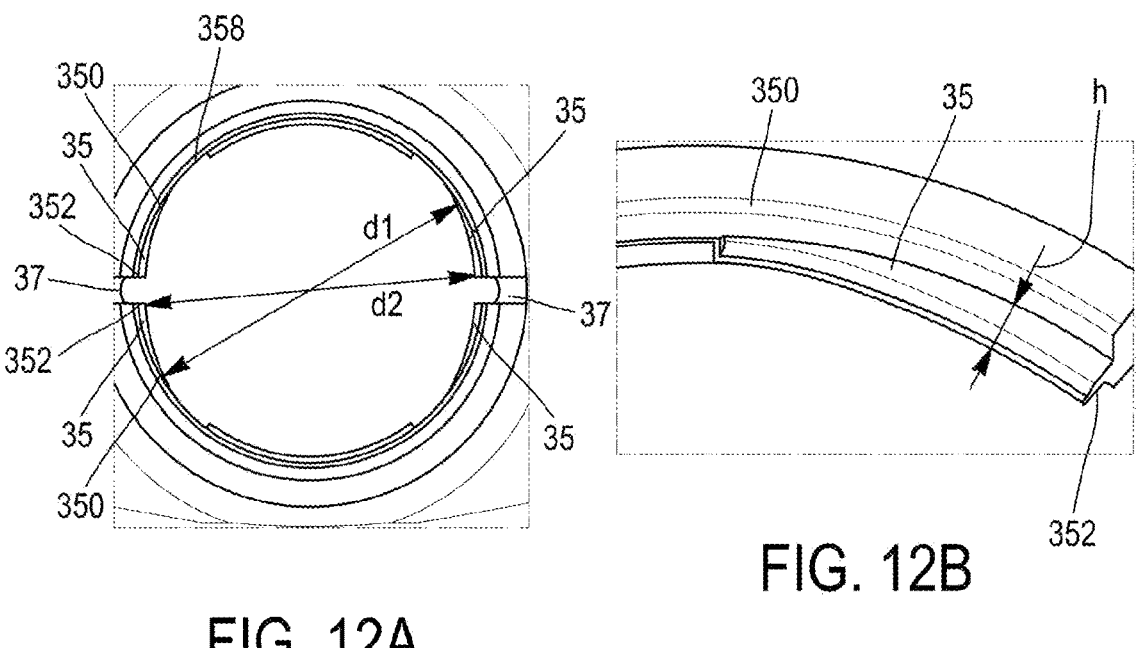
FIG. 12A
FIG. 12B
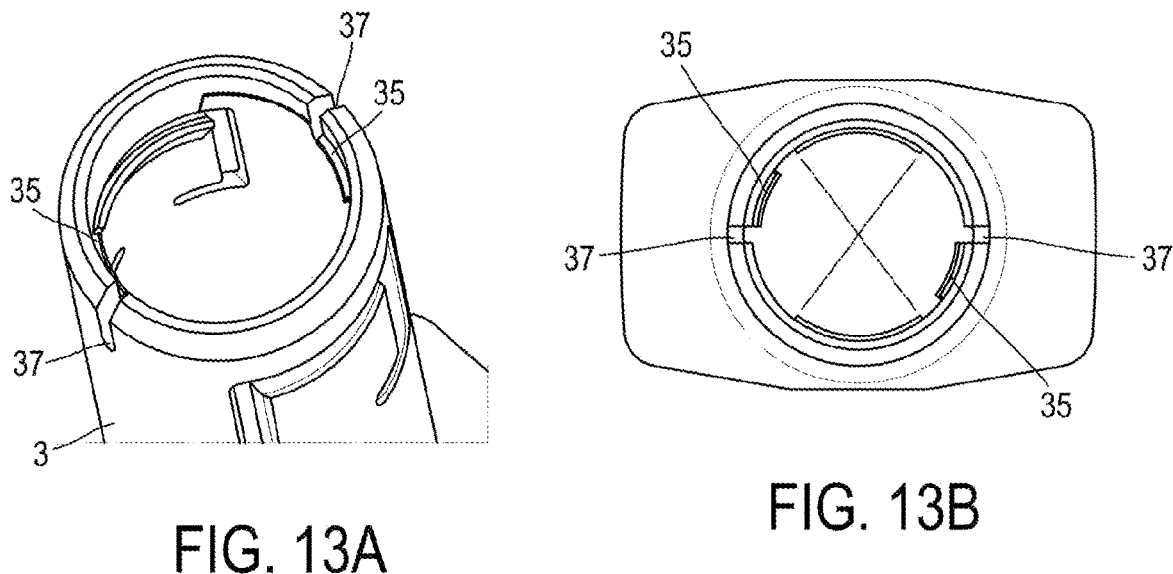
FIG. 13A
FIG. 13B

SAFETY DEVICE FOR SHIELDING AN INJECTION NEEDLE OF A MEDICAL CONTAINER, AND AN INJECTION DEVICE INCLUDING THIS SAFETY DEVICE

CROSS-REFERENCE TO RELATED APPLICATION

This application claims priority to European Patent Application No. 21306937.0 filed Dec. 24, 2021, the disclosure of which is hereby incorporated by reference in its entirety.

BACKGROUND OF THE INVENTION

Field of the Invention

The present invention relates to a safety device for mounting onto an injection device such as a prefilled or pre-fillable syringe in order to protect a user from needle stick injuries after injection of a medical product. The invention also relates to an injection device including this safety device.

Description of Related

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, with respect to the safety device or injection device of the invention, and the "proximal direction" is to be understood as meaning the opposite direction to said direction of injection, that is to say the direction towards the user's hand.

Injection devices, such as pre-fillable or prefilled syringes, usually comprise a hollow body or barrel forming a container for a medical product. This body comprises a distal end in the form of a longitudinal tip defining an axial passageway through which the medical product is expelled from the container. The distal end is equipped with a needle for injection of the medical product into an injection site.

In order to minimize the risks of needle stick injuries, injection devices may be equipped with a safety device that protects the needle after injection. Safety devices usually comprise a tubular body for receiving the syringe barrel, and a needle cover, in the form of a protective sleeve, that slides relative to the body. The needle cover has a retracted position in which the needle cover is substantially contained inside the body to allow a user to perform an injection, and an extended position in which the needle cover moves distally from the retracted position to cover the needle once the injection is completed.

There are mainly two types of safety devices: passive or active. Passive safety devices do not require the user to perform any action to ensure that the needle cover moves in the extended position and covers the needle. Thus, these passive safety devices automatically shield the needle after injection. In contrast, the active safety devices need to be activated by the user, i.e. they require the user to undertake a specific action to trigger movement of the needle cover and thus protect the needle once the injection is completed.

In active safety devices, movement of the protective sleeve from the retracted to the extended position is traditionally caused by the user exerting a distal activation force on a plunger rod of the injection device. This activation force needs to be high enough to prevent inadvertent triggering of the safety mechanism, but low enough to permit the users to easily activate the protective sleeve once the injection is completed.

Therefore, there is a need to decrease the activation force to a required minimum and to reduce the variability of this activation force.

SUMMARY OF THE INVENTION

An aspect of the invention is a safety device for mounting onto a medical container provided with a flange and an injection needle, the safety device including:
  a tubular body extending along a longitudinal axis A, the tubular body being configured to receive the medical container,
  a needle cover movable relative to said body between a retracted position, and an extended position in which the needle cover distally extends from the retracted position in order to shield the injection needle after activation of the safety device,
  a release element configured to move the needle cover from the retracted to the extended position after activation of the safety device,
  a retainer, the retainer being configured to transmit a user's activation force to the needle cover once the injection operation is completed, wherein
  the needle cover includes a distal abutment surface, said distal abutment surface abutting against a proximal abutment surface of a bump protruding from the body in the retracted position of the needle cover, wherein the body has a first axial slot extending from a distal end of the body, and the bump is circumferentially distant from said first axial slot.

The safety device of the invention allows reducing the variability of this activation force. Indeed, the bump is closer to a flexion point, thereby reducing a lever arm between this flexion point and a second end of the bump. This decrease of the lever arm enables to decrease the variability of the activation force.

The activation force may be a distal axial force. The retainer is thus configured to push the needle cover in the distal direction. The transmittal of the actuation force from the retainer to the needle cover may be due to the distal end of the retainer abutting against the proximal end of the needle cover to cause the needle cover to leave the retracted position and pass over the bump. Then the needle cover is pushed in the distal direction by the release element.

The bump may extend orthogonal to the first axial slot. The slot is configured to ease outward deformation of the body at the level of bump. The bump extends between a first end and an opposite second end. The second end is next to the first axial slot. By circumferentially distant, it is meant that a second end of the bump is circumferentially away from the first axial slot, such that a circumferential gap separates a sidewall of the first axial slot and the second end of the bump. This circumferential gap, or spatial shift, defines a shoulder between the second end of the bump and the first axial slot.

In an embodiment, the first axial slot has a proximal end, said proximal end being proximally located with regard to the bump. The first axial slot may be U-shaped.

In an embodiment, the distance between the bump and the first axial slot is defined by a central angle comprised between 5-13°.

In an embodiment, the first axial slot extends between two bumps of the body, each of said two bumps being circumferentially distant from said first axial slot. They may be separated from the first axial slot by a similar spatial shift. The two bumps may be symmetrical to each other with regard to a longitudinal plane including the longitudinal axis A and separating the first axial slot in two halves.

The safety device may further comprise some or all of the following features that help modify the activation force and reduce its variability.

In an embodiment, at least one of the proximal abutment surface and the distal abutment surface includes a chamfer configured to ease passage of the needle cover over the bump when the needle cover moves distally to the extended position. In an embodiment, the chamfer of the distal abutment surface and/or the chamfer of the bump has a frustoconical shape. In an embodiment, the proximal abutment surface of the bump and the distal abutment surface of the needle cover both include a chamfer, and the chamfer of the distal abutment surface and the chamfer of the bump are complementarily shaped. This provides a surface contact between the distal abutment surface of the needle cover and the bump of the body, instead of a line contact, thereby allowing the needle cover to easily pass over the bump and thereby further reducing the variability of the activation force. The chamfer of the distal abutment surface and/or the chamfer of the bump may be inclined between 25-70° with regard to the longitudinal axis A. In an embodiment, the chamfer of the distal abutment surface and the chamfer of the bump are inclined 45° with regard to the longitudinal axis A.

The distal abutment surface is located on a distal portion of the needle cover. The bump is located on a distal portion of the body. The needle cover includes a locking ring, said locking ring being proximally located with respect to the distal abutment surface of the needle cover.

In an embodiment, the distal abutment surface is located on a reduced thickness portion of the needle cover. A reduced section width w of the needle cover indeed enables to favor inward deformation of the needle cover when the distal abutment surface of the needle cover passes over the bump of the body. In an embodiment, this portion includes one or several axial grooves. In an embodiment, this portion has an inner diameter which is greater than an inner diameter of the rest of said needle cover. In an embodiment, this portion is the distal portion of the needle cover. Thus, the needle cover has a distal end whose inner diameter D is greater than an inner diameter of the rest of said needle cover.

The distal abutment surface may protrude from a lateral wall of the needle cover and is located on a reduced thickness portion of said lateral wall (with respect to the thickness of the rest of said lateral wall). Thus, the width of the lateral wall at the axial position of the distal abutment surface is lower than the width of the lateral wall in the rest of the needle cover. The lateral may have a constant width, except the portion of said lateral wall from which the distal abutment surface protrudes. The lateral wall may be cylindrical. The distal abutment surface, the activation ring and the locking ring are not part of the lateral wall but radially protrude from said lateral wall; thus by width of the lateral wall it is meant the width between an inner surface and an outer surface of said lateral wall, without considering the radial dimension of the distal abutment surface, activation ring or locking ring.

In an embodiment, the distal abutment surface of the needle cover is located on a radial protrusion, and the radial protrusion has reinforcing means configured to reinforce a proximal side of this radial protrusion. In an embodiment, the reinforcing means include a bulge at the proximal side of the radial protrusion. In an embodiment, the bulge circumferentially extends all around the needle cover. That is, the bulge extends 360° around the longitudinal axis A. In an embodiment, the bulge has a curved surface and is preferably teardrop shaped. In an embodiment, an axial distance from a crest to a proximal end of the radial protrusion may be greater than an axial distance from said crest to a distal end of the radial protrusion.

The proximal side of the radial protrusion is axially longer than the distal side of the radial protrusion.

In an embodiment, the bump has a cantilevered portion. The cantilevered portion of the bump is configured to flex when the needle cover passes over the bump, such that damage caused by the bump to the distal abutment surface of the needle cover is reduced, thereby improving the activation force stability. In an embodiment, the cantilevered portion of the bump extends in a lateral opening of the body. In an embodiment, the cantilevered portion extends from a first end of the bump to a lateral wall of the body. In an embodiment, a chamfer is provided at the junction between a lateral wall of the body and the cantilevered portion of the bump.

In an embodiment, the body has a first axial slot and a second axial slot, the first axial slot and the second axial slot extending on both sides of the bump. In an embodiment, the first axial slot is V-shaped and the second axial slot is U-shaped. In an embodiment, the second axial slot is longer than the first axial slot. Possibly, the first axial slot has a closed proximal end, and this closed proximal end is distally arranged with regard to the bumps. Possibly, the second axial slots have a closed proximal end, and this closed proximal end is proximally arranged with regard to the bumps. Possibly, the first axial slot and the second axial slot have an opened distal end. In an embodiment, the body comprises a locking window for accommodating a locking element of the needle cover, and the second axial slot is positioned between the locking window and the bump. In an embodiment, the body has two bumps and the first axial slot is positioned between said two bumps. More specifically, each bump has a first end and an opposite second end, and the two bumps are separated by the first axial slot extending adjacent to the second ends of said two bumps, and the body includes two second axial slots extending adjacent to the first ends of said two bumps. Possibly, the first end of the bumps coincides with an inner lateral wall of the corresponding second axial slot. Possibly, the first end of the bumps is circumferentially distant from the corresponding second axial slot.

The first axial slot and the second axial slot may have different lengths. The first axial slot may thus be axially longer or shorter than the second axial slot. The body may have two second axial slots, two bumps and the first axial slot is positioned between said two bumps, while the two bumps and said first axial slot are positioned between the two second axial slots.

In an embodiment, the bump extends in a circumferential direction according to a central angle comprised between 22.5°-45°. The longer the bump, the higher the activation force will be. Conversely, the shorter the bump, the lower the activation force will be. In an embodiment, the body includes a first axial slot and two arranged at both sides of said first axial slot, and the central angle defined by the two bumps together is between 45-90°. That is, the central angle between the first end of one of said two bumps and the first end of the other bump is between 45-90°. In an embodiment, the central angle is equal to or greater than 35°, for instance 35°-45°. This reduces the variability of the activation force. In another embodiment, the central angle is equal to or lower than 35°, for instance 22.5°-35°. This reduces the activation force. Possibly, the circumferential length of the bump may be comprised between 11 mm-12 mm, for instance 11.8 mm.

In an embodiment, the bump of the body has a first end provided with a chamfer extending in a circumferential direction. Instead of having a sharp first end, this chamfer, which extends in a circumferential direction with regard to the longitudinal axis A, enables to reduce the stress on the needle cover when the needle cover passes over the bump. In an embodiment, the chamfer is configured so that the height of the first end of the bump decreases in an outward circumferential direction. Apart from the first end, and possibly the second end, the bump may otherwise have a constant height. In an embodiment, the chamfer includes a continuously, preferably a constantly, decreasing slope. The chamfer may delimit an inclined plane. In an embodiment, the bump of the body has an opposite second end which is adjacent to a first axial slot of the body. That is, the chamfer is opposite the first axial slot. Although not illustrated, the second end of the bump may include a chamfer extending in a circumferential direction, opposite the chamfer of the first end.

By chamfer extending in a circumferential direction it should be understood that the height (radial dimension) of the first end of the bump progressively decreases, in a circumferential direction going away from the bump.

In an embodiment, the bump of the body has a first end, an opposite second end, and a decreasing height h from said second end to said first end. This progressively decreasing height permits to distribute the stress load on the needle cover such that the activation force decreases. The bump may have a curved shape between the first end and the second end. In an embodiment, the bump defines an elliptic curve in a transversal plane orthogonal to the longitudinal axis A. Preferably, the height h of the bump is continuously, preferably constantly, decreasing from the second end to the first end of the bump. In an embodiment, the body has a first axial slot, and the second end of the bump is adjacent to said first axial slot. That is, the height h of the bump decreases away from said first axial slot. The closer the first axial slot, the higher the height h of the bump is. The body may have two rotation-symmetrical bumps, and the diameter d1 between the diametrically opposite first ends of the bumps is higher than the diameter d2 between the diametrically opposite second ends of the bumps. The diameter d1 may be comprised between 10-11 mm, for instance 10.81 mm. The diameter d2 may be comprised between 10-11 mm, for instance 10.41 mm.

The bump extends circumferentially between the first end and the second end. The decreasing height permits to reduce or at least limit the needed activation force. This eases passage of the needle cover over the bump when the needle cover leaves the retracted position.

In an embodiment, the device includes only two bumps. The two bumps protrude from the body, and the two bumps have a proximal abutment surface, the distal abutment surface of the needle cover abutting against the proximal abutment surface of these only two bumps in the retracted position of the needle cover. In an embodiment, the bumps are diametrically opposite. The safety device thus includes only one pair of diametrically opposite bumps, i.e. only two bumps. In an embodiment, the bumps are rotation-symmetrical with regard to the longitudinal axis A. They may have the same length, same height, same shape.

The body may include only two first axial slots extending adjacent to one end of the bumps. The only two bumps permit to ease passage of the needle cover over said bumps when the needle cover moves from the retracted position to the extended position.

In an embodiment, the bump has a first end and an opposite second end, and the proximal abutment surface of said bump has a ramp portion, said ramp portion having a decreasing slope towards the first end of said bump. That is, the slope of the ramp portion decreases in the circumferential direction towards the first end. In an embodiment, the slope progressively, preferably continuously, decreases from the second to the first end of the bump. The closer the first end of the bump, the lower the slope of the ramp portion is. Conversely, the closer the second end of the bump, the greater the slope of the ramp portion is. In an embodiment, the axial dimension of the ramp portion is greater at the first end than at the second end of the bump. As a result, the ramp portion gradually widens towards the first end, while tapering towards the second end of the bump. The ramp portion may have a helix shape. In an embodiment, the ramp portion delimits a twisted contact surface. In an embodiment, the second end of the bump is adjacent to a first axial slot.

The slope is defined with regard to a longitudinal direction. Thus, the inclination of the ramp portion is lower and said ramp portion has a greater axial dimension at the first end of the bump (the end which is the furthest from the first axial slot) than at the second end of the bump (the end which is the closest to the first axial slot).

In an embodiment, the body has a first axial slot extending from a distal end of said body, the first axial slot having a predetermined length comprised between 1-6 mm. The lower the length of the first axial slot, the higher the activation force will be. Conversely, the higher the length of the first axial slot, the lower the activation force will be. In an embodiment, the first axial slot has a closed proximal end, and said proximal end is proximally located with regard to a proximal abutment surface of a locking window. In an embodiment, the first axial slot has a length L equal to or lower than 4.5 mm. In an embodiment, the first axial slot has a length L equal to or greater than 4.5 mm. In an embodiment, the first axial slot extends adjacent to a second end of the bump. Preferably, the body includes two diametrically opposite first axial slots. These first axial slots may be configured such that a X % decrease, respectively increase, of their length L with regard to a reference length of 4.5 mm entails a similar X % increase, respectively decrease, of the activation force. The two diametrically opposite first axial slots may have a similar length and a similar shape.

The bump, more specifically a second end of the bump, is adjacent the first axial slot. The bump is axially located between the distal end of the body and a proximal end of the first axial slot.

In an embodiment, the safety device is an active safety device.

Another aspect of the invention is an injection device including a medical container having an injection needle and a safety device having the aforementioned features, said safety device being mounted onto said medical container.

BRIEF DESCRIPTION OF THE DRAWINGS

The invention and the advantages arising therefrom will clearly emerge from the detailed description that is given below with reference to the appended drawings as follows:

FIG. 3 is a perspective view of a distal end of a needle cover of a safety device according to an embodiment of the invention, FIGS. 4A and 4B are, respectively, a front and a cross-section view of a distal end of a needle cover of a safety device according to an embodiment of the invention, FIGS. 5A and 5B are, respectively, a front and a cross-section view of a distal end of a needle cover of a safety device according to an embodiment of the invention, FIGS. 12A and 12B are, respectively, a bottom and a perspective view of a distal end of a body of a safety device according to an embodiment of the invention, FIGS. 13A and 13B are, respectively, a perspective view and a top view of a distal end of a body of a safety device according to an embodiment of the invention.

DESCRIPTION OF THE INVENTION

Figure 1:
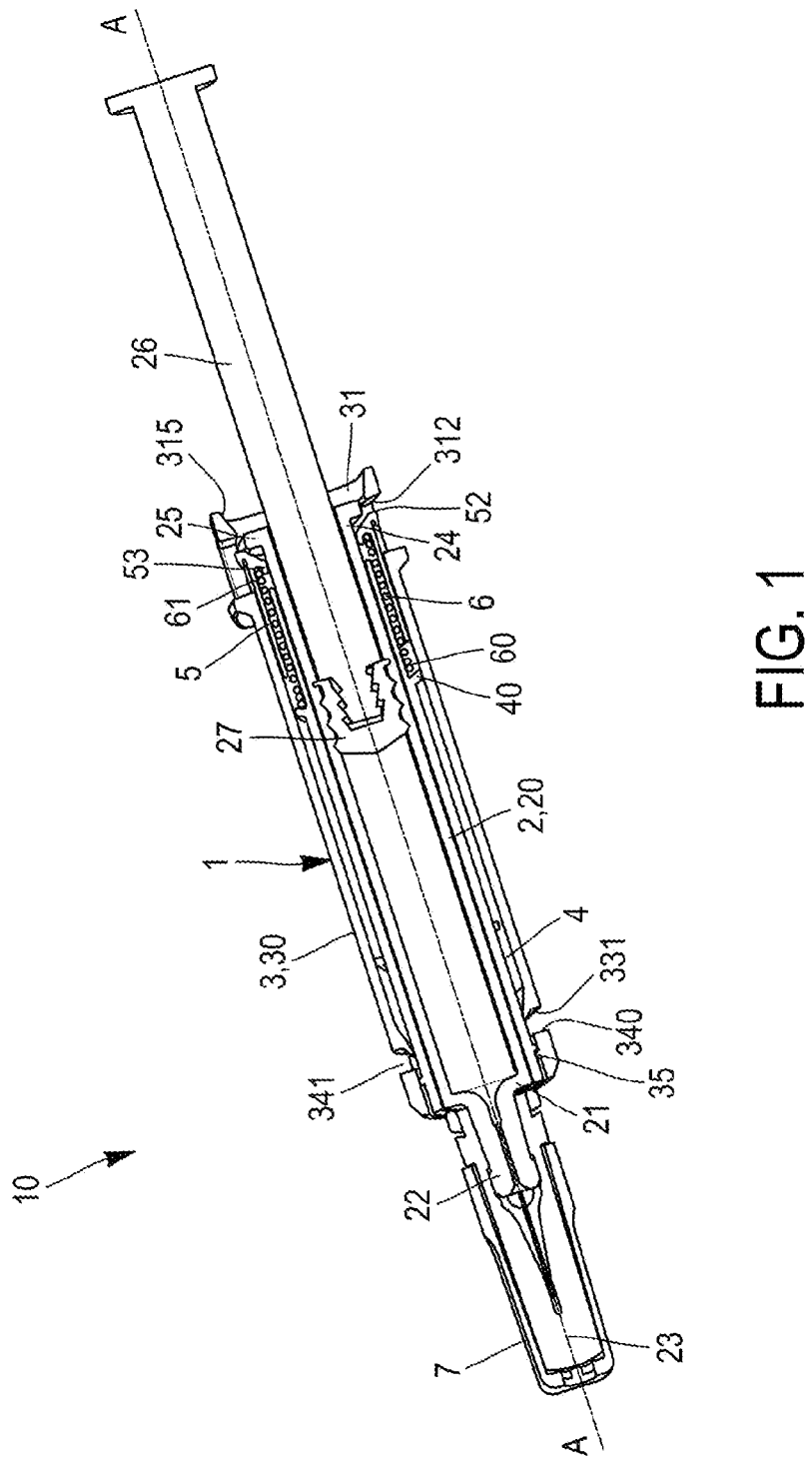
FIG. 1 is a cross-section view in a longitudinal plane of a safety device according to an embodiment of the invention, this safety device being mounted onto a medical container.

With reference to FIG. 1 is shown a safety device 1 according to an embodiment of the invention. The safety device 1 is configured to be mounted onto a medical container 2 in order to shield an injection needle 23 of this medical container 2 once an injection operation is completed. The safety device 1 may be an active safety device, where shielding of the injection needle 23 is caused by an action of the user at the end of the injection operation. This action may be a further distal push exerted by the user on a plunger rod 26 after completion of the injection operation.

The medical container 2 may be a prefilled or prefillable syringe. The medical container 2 includes a tubular barrel 20 defining a reservoir for containing a medical product. The tubular barrel 20 may be made of a plastic or a glass material. This barrel 20 has a distal shoulder 21 provided with a distal tip 22 longitudinally protruding from said shoulder 21 along a longitudinal axis A. The distal tip 22 defines an axial passageway in fluid communication with the reservoir and is equipped with an injection needle 23 for injecting the medical product in an injection site. The barrel 20 further includes an opposite opened proximal end 24 provided with a finger flange 25. The opened proximal end 24 receives a plunger rod 26 for pushing a stopper 27 located inside the barrel 20 in order to expel the medical product from the reservoir to the injection site via the distal tip 22 and the injection needle 23.

The safety device 1 includes a tubular body 3 extending along a longitudinal axis A, a needle cover 4 configured to slide along said tubular body 3 from a retracted position (see for instance FIGS. 1, 16C) to an extended position (FIGS. 16E and 16F), a release element 6 such, as a spring, for moving the needle cover 4 towards the extended position, and a retainer 5 configured to retain the release element 6, i.e. to maintain the spring, inside the safety device 1 and to transmit a distal activation force to the needle cover 4. The safety device 1 of the invention may be an active safety device 1 that requires a user to exert an actuation force on the retainer 5, and thus on the needle cover 4, in order to cause movement of the needle cover 4 from the retracted position, in which the needle cover 4 allows the injection needle 23 to enter an injection site, to the extended position, in which the needle cover 4 shields the injection needle 23 to prevent needle stick injuries. The medical container 2 may include a removable tip cap 7 for protecting and sealing the injection needle 23 before use.

Figure 2:
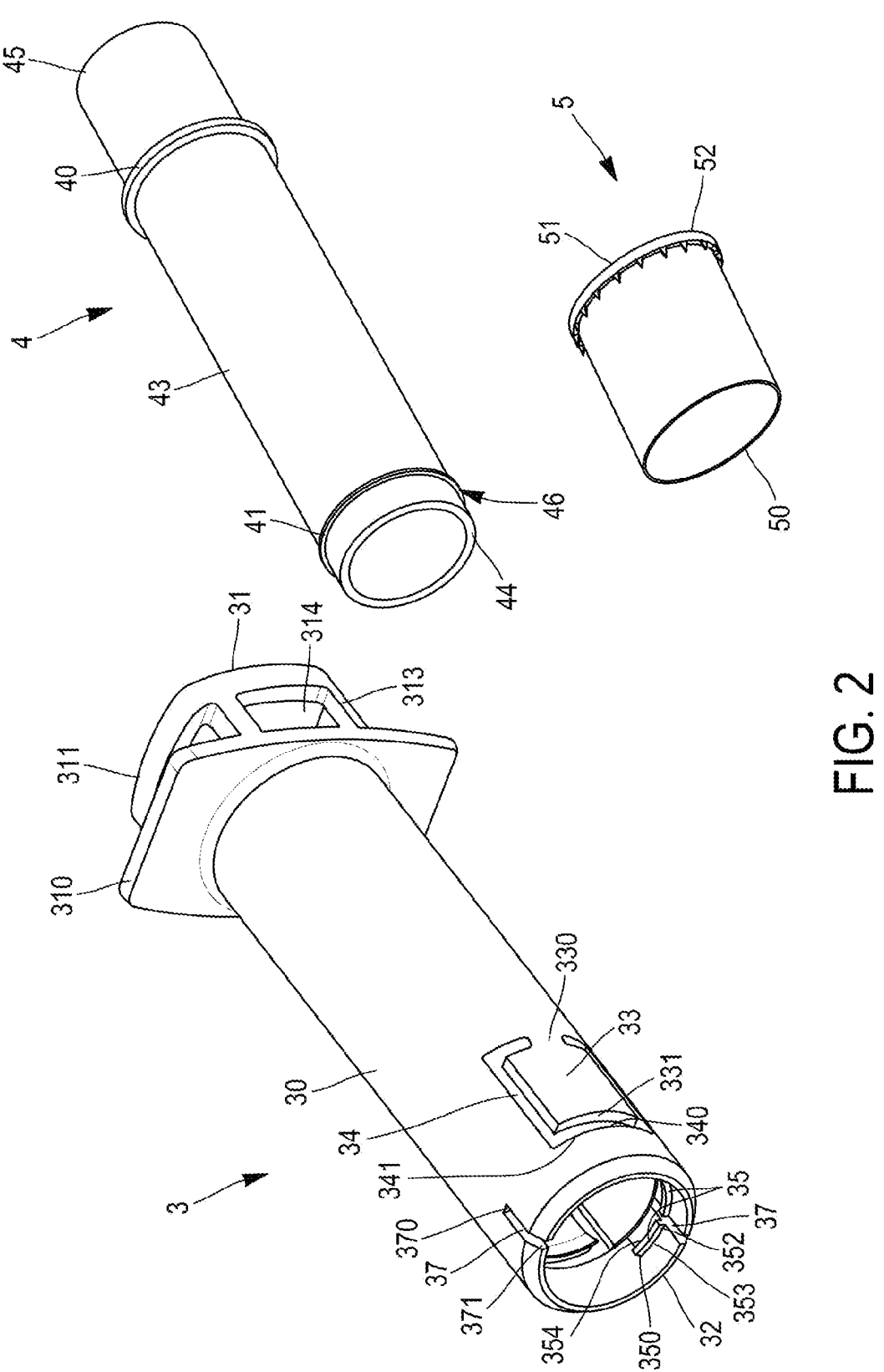
FIG. 2 is a perpsective exploded view of a body, a needle cover and a retainer of a safety device according to an embodiment of the invention.

With reference to FIG. 2, the tubular body 3 includes a lateral wall 30 defining a substantially cylindrical inner cavity for accommodating the needle cover 4, an opened proximal end 31 for allowing insertion of the medical container 2 inside the safety device 1, and an opposite opened distal end 32. The opened distal end 32 of the body 3 permits the injection needle 23, and possibly the distal tip 22 and the removable tip cap 7 to stick out the safety device 1 before use. The body 3 further includes an outward flange 310 providing support for a user's fingers. In order to secure the safety device 1 onto the medical container 2, the proximal end 31 of the body 3 may include clipping means. As illustrated in FIG. 2, the clipping means may comprise a clipping ring 311 connected to the flange 310 by axial pillars 313, and clipping windows 314 defined between the clipping ring 311, the flange 310 and the axial pillars 313. A proximal side of the clipping ring 311 forms a ramp portion 315 (FIG. 1) configured to engage the syringe flange 25 and ease deformation of the clipping ring 311 and the axial pillars 313 so that the syringe flange 25 may be inserted inside the clipping windows 314. On its distal side, the clipping ring 311 has a distal blocking surface 312 (FIG. 1) for securing the syringe flange 25 inside the clipping windows 314. The tubular body 3 of the safety device 1 is further provided with locking means for locking the needle cover 4 in the extended position. The locking means may include one or more resilient tabs 33, for instance two diametrically opposite tabs 33. These tabs 33 may each extend inside a locking window 34 located through the lateral wall 30 of the tubular body 3, said locking window 34 defining a proximal abutment surface 340 for blocking a locking element, such as a locking ring 40, of the needle cover 4 in the distal direction. The body 3 may include two diametrically opposite locking windows 34. The resilient tab 33 has a proximal end 330, which may be of reduced width, connected to the lateral wall 30 of the body 3 and an opposite free distal end provided with a distal abutment surface 331 for engaging the locking ring 40 of the needle cover 4. The distal end of the tab 33 and the proximal abutment surface 340 of the locking window 34 define a gap 341 configured to be engaged by the locking ring 40 of the needle cover 4, thereby providing a locking engagement between the body 3 and the needle cover 4 when the needle cover 4 is in the extended position.

Before activation of the safety device 1, the needle cover 4 is maintained in the retracted position. To that end, the distal portion of the tubular body 3 may comprise one or several bumps 35 protruding from an inner side of the lateral wall 30 of the tubular body 3. The distal end 32 may also comprise one pair of diametrically opposite axial slots 37 having a closed proximal end 370 and an opened distal end 371 for easing outward deformation of the distal portion of the body 3 when the device is being activated. These axial slots may be U-shaped. Each first axial slot 37 may be located at an equal distance from the locking windows 34. With reference to FIG. 2, the bumps 35 are configured to maintain the needle cover 4 in the retracted position, against the action of the spring 6, as long as the activation force is below a predetermined threshold. The bumps 35 may be in the form of a rib circumferentially extending between a first end 350 and an opposite second end 352. The second end 352 leads to one of the first axial slots 37. The bumps 35 further define a distal abutment surface 353 and an opposite proximal abutment surface 354 configured to engage a distal abutment surface 46 of an outward radial protrusion, such as an activation ring 41, of the needle cover 4. The safety device 1 may include two pairs of diametrically opposite bumps 35, i.e. four bumps 35, although the number of bumps 35 may be higher or lower than four.

Still with reference to FIG. 2, the needle cover 4 is in the form of a tubular sleeve configured to slide inside the body 3. The needle cover 4 has a lateral wall 43 defining an inner cavity for receiving the barrel 20 of the medical container 2, an opened distal end 44 and an opened proximal end 45. The needle cover 4 further includes a locking ring 40 configured to engage the locking means of the body 3 such that the needle cover 4 is locked in the extended position after being activated, and the activation ring 41 configured to engage the bumps 35 of the body 3 in order to maintain the needle cover 4 in the retracted position before activation. The activation ring 41 and/or the locking ring 40 preferably extend 360° all around the needle cover 4 to provide a reliable engagement with, respectively, the bumps 35 and the locking means of the body 3. The locking ring 40 may be located on a proximal portion of the needle cover 4, near the proximal end 45, while the activation ring 41 may be located on a distal portion of the needle cover 4, near the distal end 44. As visible in FIG. 1, a distal end 60 of the spring 6 abuts against the locking ring 40 of the needle cover 4 in order to push the needle cover 4 in the distal direction.

With reference to FIGS. 1 and 2, the retainer 5 is in the form of a cylindrical ring, including an opened distal end 50 and an opened proximal end 51 for receiving the medical container 2. The proximal end 51 has an outward circumferential rib 52 engaged in the clipping window of the body 3, and an inward circumferential rib 53 (FIG. 1) defining a recess for accommodating a proximal end 61 of the spring 6. In the retracted position of the needle cover 4, the retainer 5 retains the release element, i.e. maintains the spring 6 in a compressed condition. The distal end 50 of the retainer 5 may be configured to abut against the needle cover 4 to transmit to the needle cover 4 the activation force that the user exerts on the proximal end 51 of the retainer 5.

The safety device 1 of the invention is aimed at decreasing the value and the variability of the activation force that the user has to exert on the needle cover 4, via the retainer 5, in order to cause activation of the device, i.e. spreading of the needle cover 4 from the retracted to the extended position to safely shield the injection needle 23.

Figures 8A, 8B:
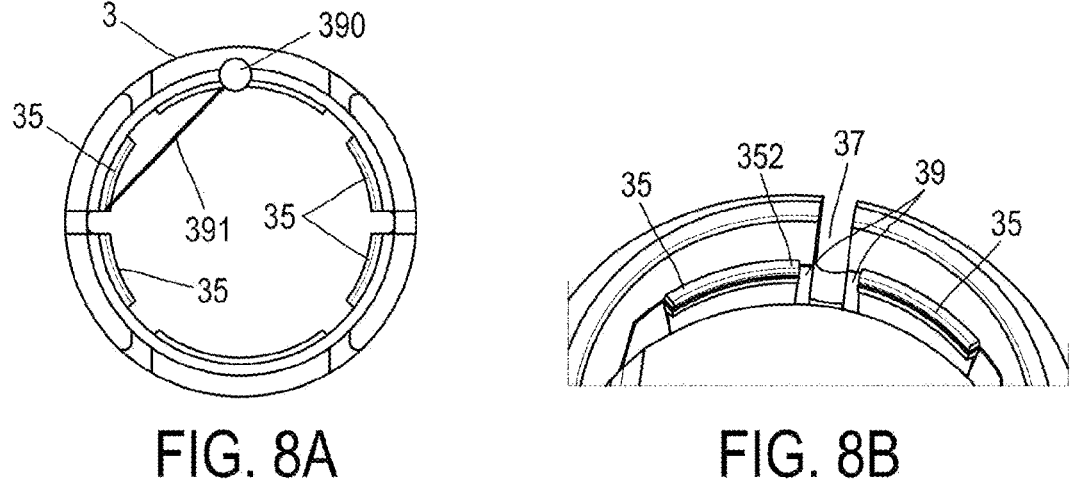
FIGS. 8A and 8B are, respectively, a bottom view and a perspective view of a distal end of a body of a safety device according to an embodiment of the invention.

To that end, with reference to FIGS. 8A and 8B, the second ends 352 of the bumps 35 may be distant from the first axial slots 37. That is, a spatial shift 39 may exist between these second ends 352 and the first axial slots 37 of the tubular body 3. The length of the bumps 35 may however be left unchanged. According to this embodiment, the bumps 35 are closer to a flexion point 390 (see FIG. 8A), thereby reducing a lever arm 391. The activation force may consequently slightly increase, but the variability of this activation force is substantially reduced. The distance between the bump 35 and the first axial slot 37 may be defined by a central angle comprised between 5-13°. In the example shown in FIG. 8B, the central angle defining the spatial shift 39 is for instance equal to 8°.

In an embodiment, the activation ring 41 of the needle cover 4 may include a chamfer 42 on its distal abutment surface 46, as shown in FIGS. 5A and 5B. The activation ring 41 thus comprises a frustoconical distal surface easing the passage of the needle cover 4 over the bumps 35 of the body 3. Accordingly, the activation force is decreased. The angle defined by the chamfer 42 with regard to the longitudinal axis may be comprised between 25-70°. In the embodiment illustrated in FIGS. 5A and 5B, the chamfer 42 defines a 45° angle from the longitudinal axis. It is contemplated that the bumps 35 of the body 3 may advantageously have a complementarily shaped chamfer on their proximal abutment surface 354, inclined for instance 45° when the chamfer 42 of the activation ring 41 of the needle cover 4 is inclined 45°. The chamfer 42 of the activation ring 41 and the chamfer of the bumps 35 may have a constant inclination all along the circumferential bumps 35 or all along the activation ring 41, i.e. may define the same angle with the longitudinal axis A. Due to the complementary shape of these chamfers, the contact between of the activation ring 41 and the bumps 35 is a surface contact, instead of a line contact. This helps reduce the activation force and its variability.

With reference to FIG. 3, the lateral wall 43 of the needle cover 4 includes a reduced thickness portion, provided with a reduced cross-section width w. The activation ring 41, and thus the distal abutment surface 46, is located on the reduced thickness portion. Preferably, this portion is the distal portion of the needle cover 4. The width w of the reduced thickness portion is lower than a width in the rest of the needle cover 4. Preferably, the reduced thickness portion defines an inner diameter D that is greater than an inner diameter in the rest of said needle cover 4. Meanwhile, the outer diameter of the needle cover 4 may be constant all along said needle cover 4, apart from the activation ring 41 and locking ring 40. The reduced thickness portion provides flexibility to the needle cover 4, thereby allowing easier deformation of the needle cover 4 when the activation ring 41 passes over the bumps 35 of the body 3. As a result, the activation force decreases. In the embodiment illustrated in FIG. 3, the reduced thickness portion may be defined by the needle cover 4 having one or several axial grooves 47, preferably located on an inner side of the lateral wall 43. The axial grooves 47 may be regularly distributed around the longitudinal axis A. They may lead to an opened distal end 460, which may coincide with the distal end 44 of the needle cover 4, and an opposite closed proximal end 461, which may be proximally located with regard to the activation ring 41. That is, the activation ring 41 is axially located between a distal end 460 and a proximal end 461 of the axial grooves 47. As visible in FIG. 3 and as mentioned above, the width w of the axial grooves 47 is lower than the width in the rest of the needle cover 4, and the inner diameter D between two diametrically opposite grooves 47 is greater than an inner diameter defined in the rest of the needle cover 4.

In the embodiment illustrated in FIGS. 4A and 4B, the activation ring 41 of the needle cover 4 comprises reinforcing means configured to reinforce a proximal side of the activation ring 41. During activation of the device, the activation ring 41 of the needle cover 4 abuts against the bumps 35 of the body 3, thereby slightly deforming the body 3 such that the body 3 opens to let the needle cover 4 pass over the bump. Yet the sharp first end 350 of the bumps 35 creates hard stress on the activation ring 41, which may in turn unwillingly deform, thereby creating variations in the activation force. The reinforcing means help prevent unwilled deformations of the activation ring 41. Thus, they reduce the variability of the activation force. In the embodiment illustrated in FIGS. 4A and 4B, the reinforcing means include a bulge 410 at the proximal side of the activation ring 41. This bulge 410 extends along the activation ring 41, preferably all along the activation ring 41, i.e. 360° around the longitudinal axis A. The axial distance from crest 413 to proximal end 414 of the activation ring 41 may be greater than the axial distance from crest 413 to distal end 415. It is noted that the crest 413 and distal end 415 of the activation ring 46 may delimit the distal abutment surface 46. Preferably, the bulge 410 has a curved surface 411 and may be, even preferably, teardrop shaped, i.e. includes a concave recess 412.

Figure 6:
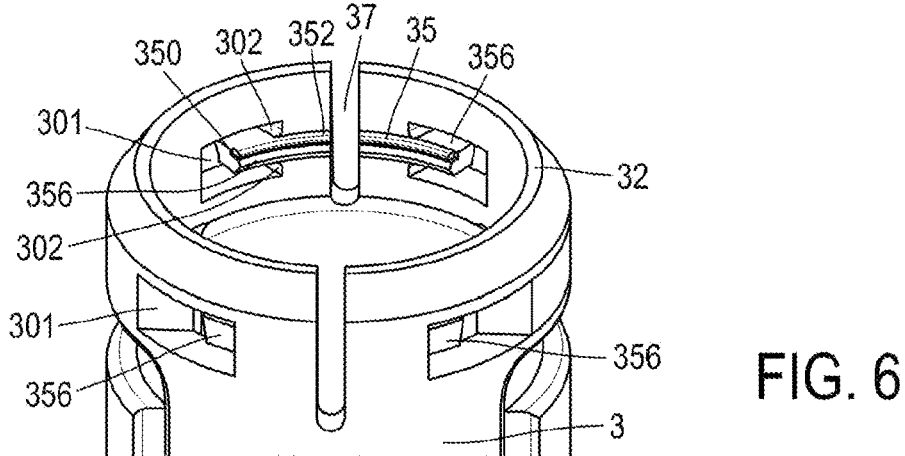
FIG. 6 is a perspective view of a distal end of a body of a safety device according to an embodiment of the invention.

With reference to FIG. 6, the bumps 35 have a cantilevered portion 356. The cantilevered portion 356 extends in a lateral opening 301 of the body 3. The openings 301 may be through-openings radially extending through the lateral wall 30 of the body 3, and they may be located at a distal portion of the body 3. In the embodiment of FIG. 6, the openings 301 do not open at the distal end 32, and they are thus axially closed, unlike the first axial slots 37. The openings 301 may be U-shaped, so that they may surround the first ends 350. Their shape and dimensions may however vary to adjust the activation force. The cantilevered portion 356 extends, preferably in the circumferential direction, from the first end 350 of the bump 35 to the lateral wall 30 of the body 3. It is observed that the first end 350 may be a free end so that the cantilevered portion 356 is a free cantilevered portion 356, which further reduces the activation force. A chamfer 302 may be provided at the junction between the lateral wall 30 of the tubular body 3 and the cantilevered portion 356 of the bumps 35. The width of the cantilevered portions 356 may be similar to the width of the lateral wall 30, and their length may be equal to or lower than half the length of the bumps 35. The cantilevered portion 356 may be resiliently deformable. The cantilevered portion 356 provides flexibility at the first ends 350 of the bumps 35, which otherwise tend to shear the activation ring 41. As a result, the deformation of the activation ring 41 is limited and the value and the variability of the activation force decrease.

Figure 7:
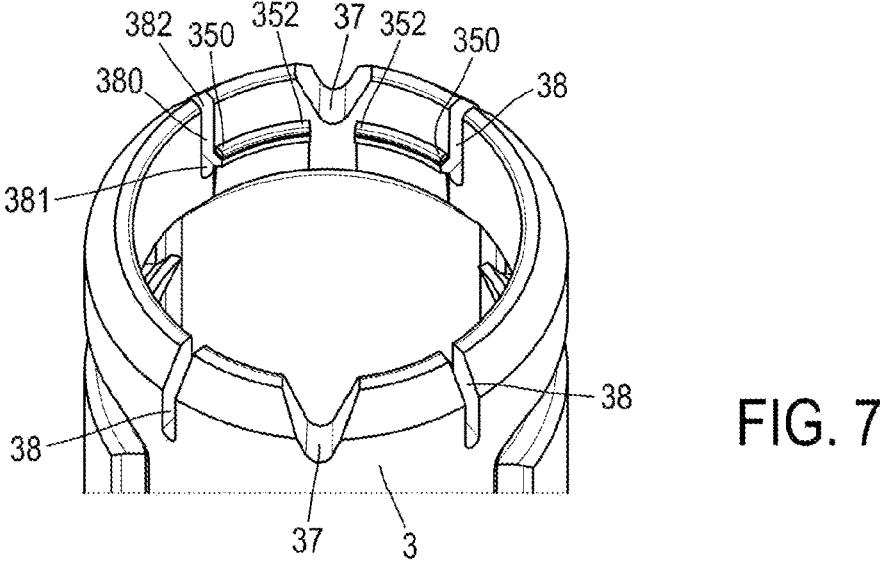
FIG. 7 is a perspective view of a distal end of a body of a safety device according to an embodiment of the invention.

According to another embodiment illustrated in FIG. 7, the tubular body 3 may include second axial slots 38 that are located at the first ends 350 of the bumps 35. That is, the first ends 350 of the bumps 35 are at the level of a lateral wall 380 of these additional axial slots 38. The second axial slots 38 may be U-shaped, or V-shaped. They provide an increased flexibility of the distal end 32 of the tubular body 3, thereby limiting the stress on the activation ring 41. This reduces the value and the dispersion of the activation force. The additional second axial slots 38 preferably have a closed proximal end 381 and an opposite opened distal end 382 which coincides with the distal end 32 of the tubular body 3. The closed proximal end 381 is advantageously located proximal to the bumps 35 to increase the flexibility. Still with reference to FIG. 7, the first axial slots 37 that extend between the second ends 352 of adjacent bumps 35 may be V-shaped or U-shaped. They may also be shortened so that the closed proximal end 381 of the axial slots 37 extends distally with regard to the bumps 35. The dimensions, number and shape of the first and second axial slots 38 may be adjusted according to a desired activation force. In the specific embodiment of FIG. 7, the body 3 has one pair of two diametrically opposite first axial slots 37 and two pairs of second axial slots 38. The two first axial slots 37 are V-shaped while the four second axial slots 38 are U-shaped. Conversely, the two first axial slots 37 may be U-shaped while the four second axial slots 38 may be V-shaped.

In the embodiment illustrated in FIGS. 9A, 9B and 10A, 10B, the length of the bumps 35 may be adjusted between a 22.5° and 45° central angle, i.e. between a 45° and 90° central angle for each pair of bumps 35, in order to modify the activation force. The central angle is measured from the first end 350 of the bump 35 to the middle of the first axial slot 37. In the embodiment shown in FIGS. 9A and 9B, the bumps 35 length may be reduced until the bumps 35 extend according to a 22.5° central angle, whereas in the embodiment shown in FIGS. 10A and 10B, the bumps 35 length may be increased such that the bumps 35 extend according to a 45° central angle. The shorter the bumps 35, the lower the activation force will be. In an embodiment, the circumferential length of the bump may be comprised between 11 mm-12 mm, for instance 11.8 mm.

Figures 9A, 9B, 10A, 10B, 11:
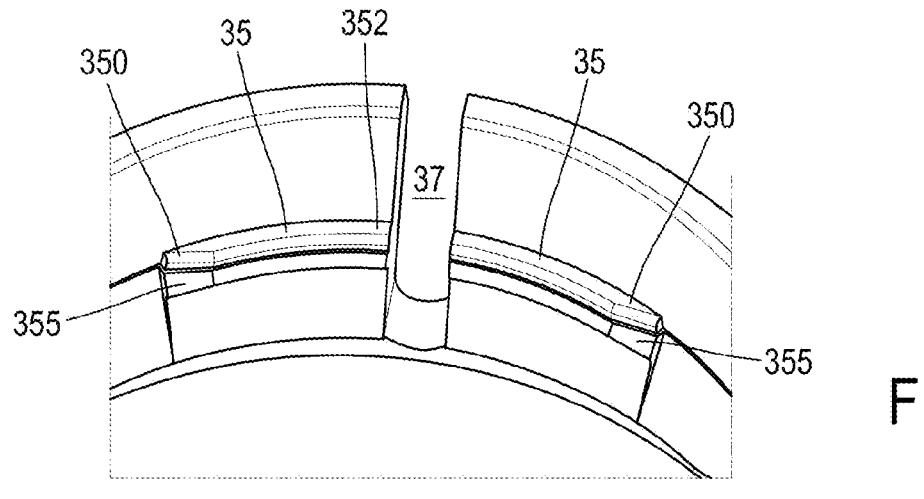
FIGS. 9A and 9B are, respectively, a bottom and a perspective view of a distal end of a body of a safety device according to an embodiment of the invention.
FIGS. 10A and 10B are, respectively, a bottom and a perspective view of a distal end of a body of a safety device according to an embodiment of the invention.
FIG. 11 is a perspective view of a distal end of a body of a safety device according to an embodiment of the invention.

With reference to FIG. 11, the first ends 350 of the bumps 35 may have a chamfer 355 in order to reduce the stress on the activation ring 41 when the activation ring 41 passes over the bumps 35. As a result, the activation force decreases. The chamfer 355 extends in a circumferential direction. In the embodiment shown in FIG. 11, only the first ends 350 of the bumps 35 are chamfered. The size of the chamfer 355 may be set according a targeted activation force.

In the embodiment illustrated in FIGS. 12A and 12B, the bumps 35 may have a varying height h. The height h is higher at the second end 352 than at the first end 350. Preferably, the height of the bumps 35 continuously decreases from their second end 352 to their first end 350, as visible in FIG. 12B. As a result, as shown in FIG. 12A, the bumps 35 may altogether define an elliptic opening 358, instead of a circular opening. That is, the bumps 35 define an elliptic curve in a plane orthogonal to the longitudinal axis A. This shape reduces the stress on the activation ring 41 and thus help decrease the activation force. As illustrated in FIG. 12A, the diameter d1 between the diametrically opposite first ends 350 of two rotation-symmetrical bumps 35 is higher than the diameter d2 between their diametrically opposite second ends 352. The diameter d1 may be comprised between 10-11 mm, for instance 10.81 mm. The diameter d2 may be comprised between 10-11 mm, for instance 10.41 mm.

With reference to FIGS. 13A and 13B, it is contemplated that the tubular body 3 may advantageously include only two bumps 35, instead of four. These two bumps 35 may be diametrically opposite. Preferably, they are symmetrical to each other with regard to a 180° rotation around the longitudinal axis A. This arrangement permits to locate the stress load exerted by the activation ring 41 on two bumps 35 only, thereby allowing the activation ring 41 to better open the distal end 32 of the body 3 and pass over the bumps 35 more easily. This enables to reduce the activation force and the variability of the activation force.

Figure 14A:
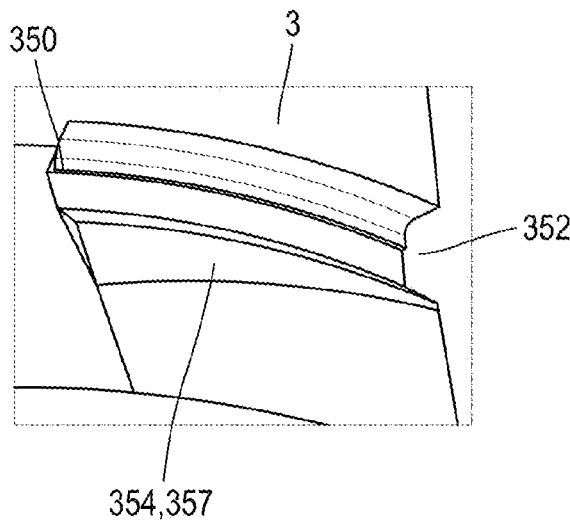
FIGS. 14A and 14B are, respectively, a perspective and a cross-section view of a distal end of a body of a safety device according to an embodiment of the invention.
Figure 14B:
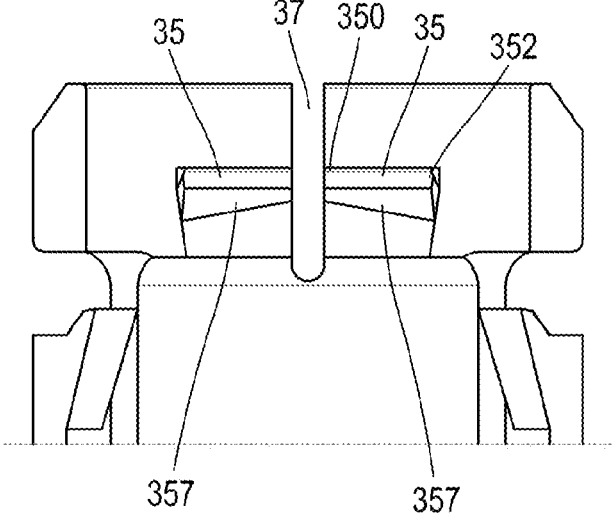

In another embodiment illustrated in FIGS. 14A and 14B, the proximal abutment surface 354 of the bumps 35 is provided with a ramp portion 357 having a helix shape. As shown in FIGS. 14A and 14B, the ramp portion 357 has a progressively decreasing slope in a circumferential direction. More specifically, the slope is higher at the second end 352 of the bump 35 and becomes lower at the first end 350. As a result, the activation force decreases. The slope may continuously decrease from the second end 352 to the first end 350 of the bump. That is, the ramp portion 357 defines with the longitudinal axis A a lower angle at the second end 352 of the bumps 35 than at their first end 350. For instance, the ramp portion 357 is inclined 45° at the second end 352 of the bumps 35, and 70° at their first end 350. The axial dimension of the ramp portion 357 may accordingly be longer at the first ends 350 of the bumps 35 than at their second ends 352. Having a steeper ramp portion 357 at the second ends 352 of the bumps 35 permits the bumps 35 to maintain the activation ring 41 and thus the needle cover 4 in the retracted position against the action of the spring 6 as long as the needle cover 4 is not activated.

Figure 15A:
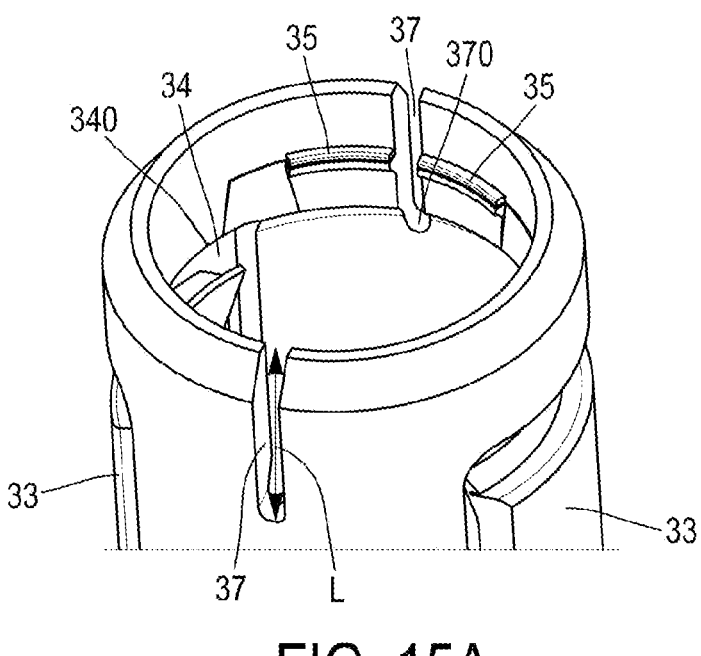
FIGS. 15A and 15B are, respectively, a perspective view and a side view of a distal end of a body of a safety device according to an embodiment of the invention.
Figure 15B:
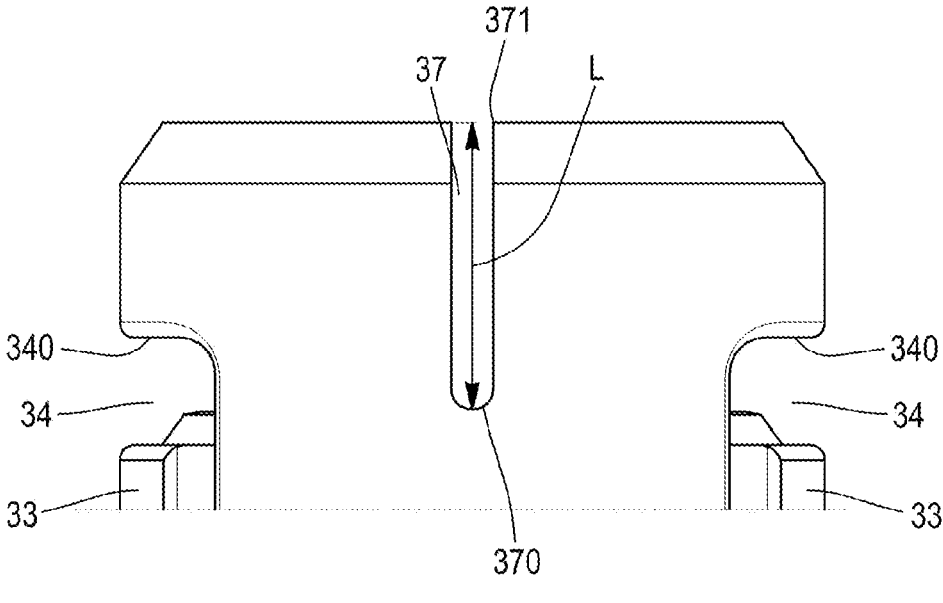

With reference to FIGS. 15A and 15B, it is contemplated the first axial slots 37 may extend such that their closed proximal end 370 is located proximally beyond the proximal abutment surface 340 of the locking windows 34, and possibly at the level of or proximally beyond the distal end of the resilient tabs 33 of the tubular body 3. This increased length of the axial slots 37 increases the flexibility of the distal end 32 of the tubular body 3, thereby decreasing the required activation force. For instance, the first axial slots 37 may have a length L comprised between 1-6 mm. The lower the length L of the first axial slots 37, the higher the activation force will be. Conversely, the higher the length L of the first axial slots 37, the lower the activation force will be. It has been observed that a X % increase (or decrease) of the length L with regard to a reference length of 4.5 mm allows a similar X % decrease (or increase) of the activation force. The first axial slots 37 are thus advantageously configured such that a X % decrease, respectively increase, of their length with regard to a length reference of 4.5 mm entails a similar X % increase, respectively decrease, of the activation force. In a possible embodiment, the first axial slots 37 have a length L lower than 4.5 mm to increase the activation force. Alternatively, the first axial slots 37 have a length L greater than 4.5 mm to decrease the activation force. For instance, tests have shown a 11% increase of the length (i.e. length of 4.995 mm) of the first axial slots allows a corresponding 11% decrease of the activation force. The shape and dimensions of the first axial slots 37 may accordingly be set in accordance with a predetermined activation force to reach.

The operation of the safety device 1 of the invention will now be described with reference to FIGS. 16A to 16F.

Figure 16A:
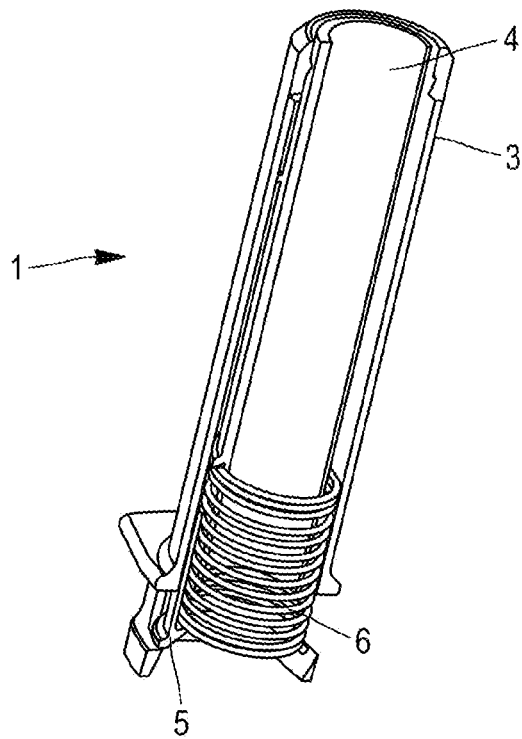
FIGS. 16A to 16F are partial cross-section views illustrating different steps of the operation of a safety device according to an embodiment of the invention.

In FIG. 16A, the device 1 is not activated. The needle cover 4 is in its retracted position, within the tubular body 3. The safety device 1 may be mounted onto a medical container 2 provided with an injection needle 23.

Figure 16B:
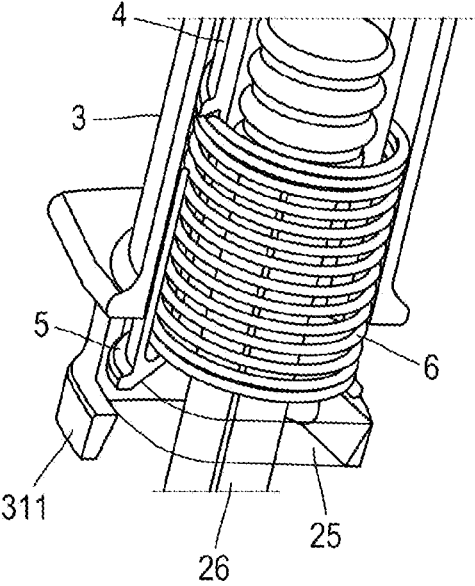

In FIG. 16B, a medical container 2 is inserted inside the tubular body 3, via the proximal end 31 of the tubular body 3. The flange 25 of the medical container 2 is clipped behind the clipping ring 311 of the tubular body 3 and comes in abutment against the retainer 5. The user may perform the injection.

Figure 16C:
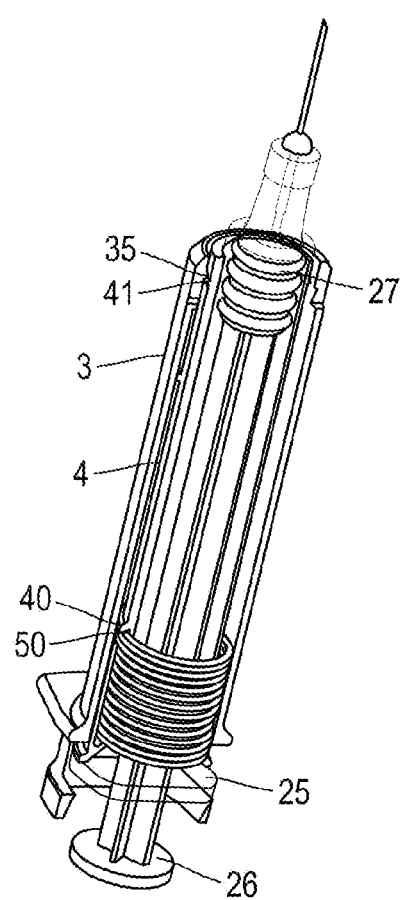

In FIG. 16C, once the injection is completed, the user needs to apply a further distal pushing force on the plunger rod 26 in order to activate the safety device 1. This pushing activation force causes the syringe flange 25 to push the retainer 5 in the distal direction. As a result, the distal end 50 of the retainer 5 abuts against the needle cover 4 and pushes the needle cover 4 forward. The activation ring 41 of the needle cover 4 therefore abuts against the bumps 35 of the tubular body 3.

Figure 16D:
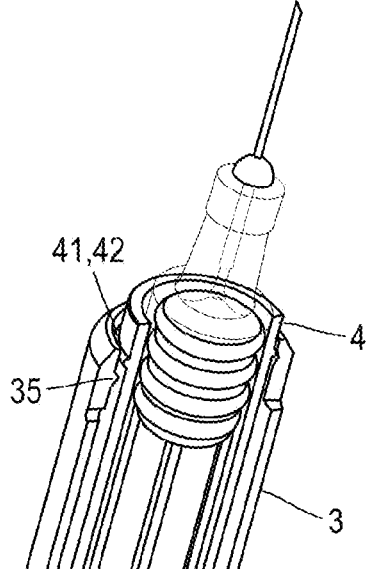

In FIG. 16D, the activation ring 41 passes over the bumps 35 of the tubular body 3. Since the bumps 35 are distant from the adjacent first axial slots 37, due to the circumferential shift 39, the variability of the activation force is decreased.

Figure 16E:
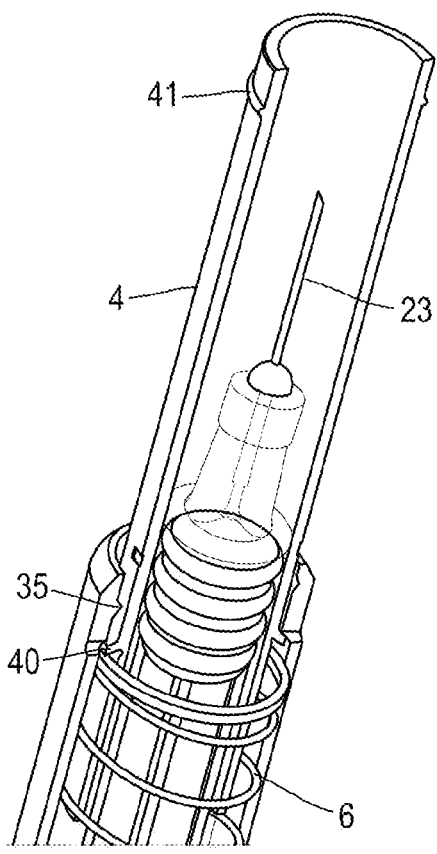

In FIG. 16E, the needle cover 4 is no longer maintained in the retracted position because the activation ring 41 has passed over the bumps 35 of the tubular body 3. Accordingly, the spring 6 moves the needle cover 4 is the distal direction until the needle cover 4 reaches the extended position, in which the needle 23 safely shields the injection needle 23.

Figure 16F:
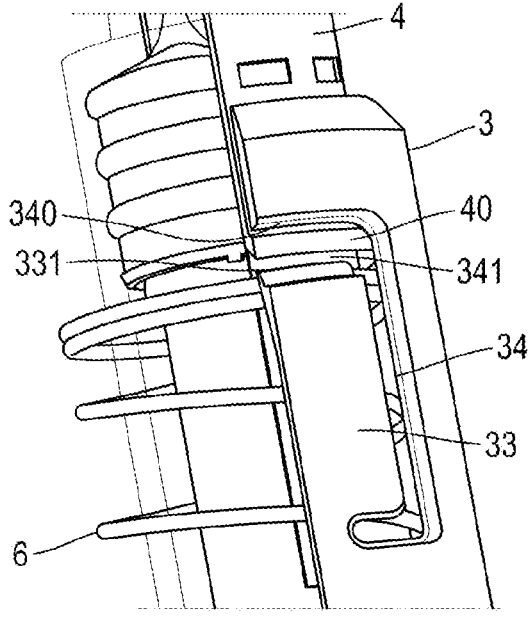

In FIG. 16F, the locking ring 40 of the needle cover 4 engages the gap 341 defined by the locking window 34 and the resilient tabs 33. The needle cover 4 cannot move further in the distal direction because the locking ring 40 abuts against the proximal abutment surface 340 of the locking window 34. The needle cover 4 cannot either move back in the proximal direction, because the locking ring 40 would abut against the distal abutment surface 331 of the resilient tab. As a result, the safety device 1 prevents needle stick injuries.

The invention claimed is:

1. A safety device for mounting onto a medical container provided with a flange and an injection needle, the safety device comprising:
   a tubular body extending along a longitudinal axis, the tubular body being configured to receive the medical container,
   a needle cover movable relative to said body between a retracted position, and an extended position in which the needle cover distally extends from the retracted position in order to shield the injection needle after activation of the safety device,
   a release element configured to move the needle cover from the retracted position to the extended position after activation of the safety device,
   a retainer, the retainer being configured to transmit an activation force applied to the retainer in a distal axial direction to the needle cover once an injection operation is completed, such that the activation force transmitted to the needle cover causes the needle cover to move from the retracted position to the extended position,
   wherein the needle cover comprises a distal abutment surface, said distal abutment surface abutting against a proximal abutment surface of a bump protruding from a distal portion of the body in the retracted position of the needle cover, and
   wherein the body has a first axial slot extending from a distal end of the body, the first axial slot has a proximal end, said proximal end being proximally located with regard to the bump, and the bump is circumferentially distant from said first axial slot.

2. The safety device of claim 1, wherein the distance between the bump and the first axial slot is defined by a central angle comprised between 5°-13°.

3. The safety device of claim 1, wherein the bump comprises two bumps and the first axial slot extends between the two bumps of the body, each of said two bumps being circumferentially distant from said first axial slot.

4. The safety device of claim 1, wherein at least one of the proximal abutment surface and the distal abutment surface comprises a chamfer configured to ease passage of the needle cover over the bump when the needle cover moves distally to the extended position.

5. The safety device of claim 1, wherein the distal abutment surface is located on a reduced thickness portion of the needle cover.

6. The safety device of claim 1, wherein the distal abutment surface of the needle cover is located on a radial protrusion of the needle cover, and the radial protrusion has reinforcing means configured to reinforce a proximal side of this radial protrusion.

7. The safety device of claim 1, wherein the bump has a cantilevered portion.

8. The safety device of claim 1, wherein the body has the first axial slot and a second axial slot, the first axial slot and the second axial slot extending on both sides of the bump.

9. The safety device of claim 1, wherein the bump extends in a circumferential direction according to a central angle comprised between 22.5°-45°.

10. The safety device of claim 1, wherein the bump of the body has a first end provided with a chamfer extending in a circumferential direction.

11. The safety device of claim 1, wherein the bump of the body has a first end, an opposite second end, and a decreasing height from said second end to said first end.

12. The safety device of claim 1, wherein the bump comprises only two bumps.

13. The safety device of claim 1, wherein the bump has a first end and an opposite second end, and the proximal abutment surface of said bump has a ramp portion, said ramp portion having a decreasing slope towards the first end of said bump.

14. The safety device of claim 1, wherein the body has the first axial slot extending from a distal end of said body, the first axial slot having a predetermined length comprised between 1 mm-6 mm.

15. An injection device comprising a medical container having an injection needle and the safety device of claim 1, said safety device being mounted onto said medical container.

\* \* \* \* \*